(12) United States Patent
Hague

(10) Patent No.: US 8,575,449 B2
(45) Date of Patent: Nov. 5, 2013

(54) COTTON VARIETY FM 9063B2F

(75) Inventor: Steve Hague, College Station, TX (US)

(73) Assignees: Bayer CropScience AG, Monheim (DE); Cotton Seed International Proprietary Limited, New South Wales (AU)

( * ) Notice: Subject to any disclaimer, the term of this patent is extended or adjusted under 35 U.S.C. 154(b) by 1396 days.

(21) Appl. No.: 11/715,055

(22) Filed: Mar. 7, 2007

(65) Prior Publication Data

US 2008/0222749 A1 Sep. 11, 2008

(51) Int. Cl.
*A01H 5/00* (2006.01)
*A01H 5/10* (2006.01)
*A01H 4/00* (2006.01)
*A01H 1/00* (2006.01)
*C12N 15/82* (2006.01)

(52) U.S. Cl.
USPC ........... 800/314; 800/260; 800/266; 800/268; 800/269; 800/270; 800/300; 800/301; 800/302; 435/421; 435/427

(58) Field of Classification Search
USPC ......... 800/260, 266, 268, 269, 270, 295, 314, 800/300–302; 435/410, 421, 427
See application file for complete search history.

(56) References Cited

U.S. PATENT DOCUMENTS 6,982,369 B2 * 1/2006 Green et al. ................. 800/314

FOREIGN PATENT DOCUMENTS

WO WO 2010/015423 * 2/2010

OTHER PUBLICATIONS

Dow AgroSciences, Risk assessment and risk management plan, DIR 040/2003, Nov. 2003, p. 25, paragraph 115.*
Muzzi. Delta Farm Press, Oct. 6, 2000.*
Cerny et al. WO 2004/072235, Aug. 26, 2004.*
Poehlman et al. Breeding Field Crops, 4th ed., 1995, Chapter 9, pp. 172-175.*
USDA APHIS Petition 02-042-01p dated Feb. 8, 2002.
USDA APHIS Petition 03-036-01p dated Jan. 31, 2003.
USDA APHIS Petition 03-36-02p dated Jan. 31, 2003.
USDA APHIS Petition 03-155-01p dated Jun. 3, 2003.

* cited by examiner

*Primary Examiner* — David T Fox
*Assistant Examiner* — Keith Robinson
(74) *Attorney, Agent, or Firm* — Buchanan Ingersoll & Rooney PC

(57) ABSTRACT

The cotton variety FM 9063B2F is disclosed. The invention relates to seeds, plants, plant cells, plant tissue, harvested products and cotton lint as well as to hybrid cotton plants and seeds obtained by repeatedly crossing plants of variety FM 9063B2F with other plants. The invention also relates to plants and varieties produced by the method of essential derivation from plants of FM 9063B2F and to plants of FM 9063B2F reproduced by vegetative methods, including but not limited to tissue culture of regenerable cells or tissue from FM 9063B2F.

36 Claims, No Drawings

COTTON VARIETY FM 9063B2F

FIELD OF THE INVENTION

This invention is in the field of plant breeding and relates to a variety of cotton designated as FM 9063B2F, its essentially derived varieties and the hybrid varieties obtained by crossing FM 9063B2F as a parent line with plants of other varieties or parent lines.

BACKGROUND OF THE INVENTION

The invention is in the field of plant breeding in the cotton species *Gossypium hirsutum*. Cotton is an important fiber producing crop. The crop is commonly reproduced by self pollination and fertilization. This way of sexual reproduction facilitates the preservation of plant and variety characteristics during breeding and seed production. The agronomic characteristics which are necessary for producing a healthy, good yielding crop are to be combined with characteristics or traits for cotton fiber of an excellent quality. Due to the complexity of the genetic basis, the interactions between genes—dependent on the position of the genes in the genome and the interaction between the genetic composition—the genotype—and the environment, the expression of said genotype in the phenotype—the eventual plant variety—is unpredictable for the person, or the ordinary plant breeder, skilled in the art. The breeder can only apply his skills on the phenotype and not, or in a very limited way, on the level of the genotype. Due to this phenomenon a particular plant breeder cannot breed the same variety twice using the same parents and the same methodology, which renders the newly bred variety as an unexpected result of the breeding process. Each variety contains a unique combination of characteristics. By carefully choosing the breeding parents, the breeding and selection methods, the testing layout and testing locations, the breeder can aim at a particular variety type. Before the invention—the new variety—can be released in practice, it is often tested in special comparative trials with other existing varieties in order to determine whether the new invention meets the required expectations.

SUMMARY OF THE INVENTION

The invention relates to seeds, plants, plant cells and part of plants, cotton lint or fiber, and cotton textile of cotton variety FM 9063B2F as well as to hybrid cotton plants and seeds obtained by repeatedly crossing plants of FM 9063B2F with other cotton plants. The invention relates also to plants and varieties produced by the method of derivation or essential derivation from plants of FM 9063B2F and to plants of FM 9063B2F reproduced by vegetative methods, including but not limited to regeneration of embryogenic cells or tissue of FM 9063B2F.

DESCRIPTION OF THE INVENTION

The invention has been obtained by a general breeding process comprising the following steps (for reference see chapter 11 of Briggs and Knowles 1967, titled "Breeding self-pollinated crops by hybridization and pedigree selection"):

Parent plants, which have been selected for good agronomic and fiber quality traits are manually crossed in different combinations. The resulting F1 (Filial generation 1) plants are self fertilized and the resulting F2 generation plants, which show a large variability on account of optimal gene segregation, are planted in a selection field.

These F2 plants are observed during the growing season for health, growth vigor, plant type, plant structure, leaf type, stand ability, flowering, maturity, seed yield, boll type, boll distribution, boll size, fiber yield and fiber quality. The selected plants are harvested and the bolls analyzed for fiber characteristics and the seed cleaned and stored. The next growing seasons this procedure is repeated, whereby the selection and testing units increase from individual plants in the F2, to multiple plant containing 'lines' (descending from one mother plant) in the F5 and the number of units decrease from approximately 2500 plants in the F2 to 20 lines in the F5 by selecting about 10-20% of the units in each selection cycle.

The increased size of the units, whereby more seed per unit is available, allows the selection and testing in replicated trials on more than one location with a different environment and a more extensive and accurate analyzing of the fiber quality.

The lines or candidate varieties become genotypically more homozygous and phenotypically more homogeneous by selecting similar plant types within a line and by discarding the so called off-types from the very variable F2 generation on to the final F7 or F8 generation.

Depending on the intermediate results the plant breeder may decide to vary on the procedure as described above: e.g., accelerating the process by testing a particular line earlier or retesting a line another year. He may also select plants for further crossing with existing parent plants or with other plants resulting from the current selection procedure.

By the method of recurrent backcrossing, as described by Briggs and Knowles 1967 in chapter 13, titled "The backcross method of breeding", the breeder can introduce a specific trait or traits into an existing valuable line or variety, while otherwise preserving the unique combination of characteristics of this line or variety. In this crossing method the valuable parent is recurrently used to cross it 2 or 3 times with each resulting backcross F1, followed by selection of the recurrent parent plant type, until the phenotype of the resulting F1 is similar or almost identical to the phenotype of the recurrent parent with the addition of the expression of the desired trait or traits.

This method of recurrent backcrossing eventually results in an essentially derived variety, which is predominantly derived from the recurrent parent or initial variety. This method can therefore also be used to get as close as possible to the genetic composition of an existing successful variety, while compared to the recurrent parent the essentially derived variety retains a distinctive trait—which can be any phenotypic trait—, with the intention to profit from the qualities of that successful initial variety.

Depending on the number of backcrosses and the efficacy of the selection of the recurrent parent plant type and genotype, which can be supported by the use of molecular markers as described by Stam, 2003, the genetic conformity with the initial variety of the resulting essentially derived variety may vary between 90% and 100%.

Except via recurrent backcrossing as described here above such essentially derived variety may also be obtained by the selection from an initial variety of an induced or natural occurring mutant plant, or of an occurring variant (off-type) plant, or of a somaclonal variant plant, or by genetic transformation of regenerable plant tissue or embryogenic cell cultures of the said initial variety by methods well known to those skilled in the art, such as for example Agrobacterium-mediated transformation as described by Sakhanokho et al, 2004, Reynaerts et al 2000, Umbeck et al 1988 and others._

Examples of transgenic Events transformed in this way are "LLCotton25" (expressing a bar coding sequence from Streptomyces hygroscopicus encoding phosphinothricin-acetyl-transferase, operably linked to a cauliflower mosaic virus 35S promoter and 3'untranslated region from a nopaline synthase gene), USDA-APHIS petition 02-042-01 p, "Cot 102", USDA-APHIS petition 03-155-01p, and "281-24-236", USDA-APHIS petition 03-036-01 p combined with "3006-210-23", USDA-APHIS petition 03-036-02p. An "Event" is defined as a (artificial) genetic locus that, as a result of genetic engineering, carries a foreign DNA comprising at least one copy of the gene(s) of interest.

The plants so selected or transformed retain the unique combination of characteristics of 9063B2F, except for the different expression of one or two or three or four or five characteristics changed by the selection of the mutant or variant plant or the one or two or three or four or five different characteristics added by the genetic transformation.

The product of essential derivation is an essentially derived variety, which is, except for the one, or two, or three, or four, or five, distinctive characteristics, which characteristics are different as the result of the act of derivation, characterized by the same combination of expression of the characteristics in its phenotype as in the phenotype of the initial variety, which same combination of expression results from the genotype that is nearly identical or almost identical or similar to the genotype of the initial variety. Plants of the essentially derived variety can be used to repeat the process of essential derivation. The result of this process is also a variety essentially derived from said initial variety.

In the process of derivation from cotton variety FM 9063B2F, plants of FM 9063B2F are used, in order to profit from the unique combination of characteristics of FM 9063B2F, as a source of variation in a breeding program in creating FM 9063B2F progeny plants by crossing plants of FM 9063B2F with other, different or distinct cotton plants, and further selfing or crossing these progeny plants with other, distinct plants and subsequent selection of derived progeny plants. The process of crossing FM 9063B2F derived progeny plants with itself or other distinct cotton plants and the subsequent selection in the resulting progenies can be repeated up to 7 times in order to produce FM 9063B2F derived cotton plants.

One embodiment of this invention relates to plants, seeds, plant cells and parts of plants of the cotton variety FM 9063B2F. Representative seeds of this variety have been deposited under rule 37CFR1.809.

Another embodiment of this invention relates to seeds, plants, plant cells and part of plants of cotton varieties that are essentially derived from FM 9063B2F, being essentially the same as this invention by expressing the unique combination of characteristics of FM 9063B2F, including the herbicide resistance of FM 9063B2F, except for one, or two, or three, or four, or five, characteristics being different from the characteristics of FM 9063B2F as a result of the act of derivation.

Another embodiment of this invention is the reproduction of plants of FM 9063B2F by the method of tissue culture from any regenerable plant tissue obtained from plants of this invention. Plants so reproduced express the specific combination of characteristics of this invention and fall within its scope. During one of the steps of the reproduction process via tissue culture somaclonal variant plants may occur, which plants can be selected as being distinct from this invention, but still fall within the scope of this invention as being essentially derived from this invention.

Again another embodiment of this invention is the production of a hybrid variety, by the well known method of repeatedly crossing plants of FM 9063B2F with plants of a different variety or varieties or with plants of a non-released line or lines. In practice 3 different types of hybrid varieties may be produced (see for reference chapter 18 of Briggs and Knowles 1967 titled "Hybrid varieties"):

The "single cross hybrid" produced by 2 different lines, the "three way hybrid", produced by 3 different lines such that first the single hybrid is produced by using 2 out of the 3 lines followed by crossing this single hybrid with the third line, and the "four way hybrid" produced by 4 different lines such that first 2 single hybrids are produced using the lines 2 by 2, followed by crossing the 2 single hybrids so produced.

Each single, three way or four way hybrid variety so produced and using FM 9063B2F as one of the parent lines contains an essential contribution of FM 9063B2F to the resulting hybrid variety and falls within the scope of this invention.

Cotton lint or fiber produced by the plants of this invention and by plants reproduced from this invention and by plants essentially derived from this invention have the unique combination of the quality characteristics of FM 9063B2F and fall within the scope of this invention. The final textile produced form the unique fiber of FM 9063B2F also falls within the scope of this invention.

All literature and references cited are incorporated by reference in this description.

Example 1

Seeds were obtained from plants finally selected in the process of breeding the new variety "FM 9063B2F". A sample of 2500 seeds of FM 9063B2F was deposited under the provisions of the Budapest Treaty on the International Recognition of the Deposit of Micro-organisms for the Purposes of Patent Procedure, and pursuent to rules 37 C.F.R. §1.801-.809, in the American Type Culture Collection (10801 University Blvd., Manassas, Va. 20110-2209, USA) on Jan. 30, 2012 and has been assigned ATCC Patent Deposit Designation PTA-12471.

Applicants hereby waive any restrictions on the public availability of the deposited material from the NCIMB, once a US patent has been granted on this application. However, Applicants have no authority to waive any restrictions imposed by law on the transfer, importation or (commercial) use of biological material. The Applicant does not waive any infringement of its rights granted under a patent on this application, or under the Plant Variety Protection Act (7 USC 2321 et seq.).

Seeds of the variety FM 9063B2F, of which a representative sample has been deposited, were planted, together with seeds of cotton variety FM 958 and PM HS 26 as reference varieties, in field trials at 2 locations, as mentioned hereunder. The results as shown in Table 1 and 2 were obtained from a pooled analysis of the data from these two trials:

BCSI Research Station, Leland Miss., 2004. Conditions: field grown irrigated trial with conventional management.

Trial design: 5 entry trial in a row and column design with six replicates and 14 m plots. Measurements on 10 plants from each plot.

Analysis of variance procedures were used to obtain least significant difference statistics at the 1% level.

The description as mentioned in Table 1 reflects the average expression of the characteristics of FM 9063B2F on these locations in 2005/2006. This expression can be different on other locations and/or in other years. The sample that has been deposited represents the variety and this sample can be analyzed for the expression of its phenotypic characteristics at any time and at any location.

TABLE 1

Characteristics of FM 9063B2F

| description of characteristic | possible expression/note | Variety FM 9063B2F | FM 960BR |
|---|---|---|---|
| General Plant Type | | | |
| Plant Habit | spreading, intermediate, compact | Compact | Compact |
| Foliage | sparse, intermediate, dense | Intermediate | Intermediate |
| Stem Lodging | lodging, intermediate, erect | Erect | Erect |
| Fruiting Branch | clustered, short, normal | Short | Short |
| Growth | determinate, intermediate, indeterminate | Intermediate | Intermediate |
| Leaf color | greenish yellow, light green, medium green, dark green | Medium Green | Medium Green |
| Boll Shape | Length < Width, L = W, L > W | Length > Width | Length > Width |
| Boll Breadth | broadest at base, broadest at middle | Middle | Middle |
| Maturity | date of 50% open bolls | Sep. 22 | Sep. 27 |
| Plant | | | |
| cm. to first Fruiting Branch | from cotyledonary node | 16.1 | 16 |
| No. of nodes to 1st Fruiting Branch | excluding cotyledonary node | 6.4 | 6.3 |
| Mature Plant Height in cm. | cotyledonary node to terminal | 83.8 | 83.6 |
| Leaf: upper most, fully expanded leaf | | | |
| Type | normal, sub-okra, okra, super-okra | Normal | Normal |
| Pubescence | absent, sparse, medium, dense | Sparse | Sparse |
| Nectaries | present, absent | Present | Present |
| Stem Pubescense | glabrous, intermediate, hairy | Intermediate | Intermediate |
| Glands (Gossypol) | absent, sparse, normal, more than normal | | |
| Leaf | | Normal | Normal |
| Stem | | Normal | Normal |
| Calyx lobe | (normal is absent) | Absent/Normal | Absent/Normal |
| Flower | | | |
| Petals | cream, yellow | Cream | Cream |
| Pollen | cream, yellow | Cream | Cream |
| Petal Spot | present, absent | Absent | Absent |
| Seed | | | |
| Seed Index | g/100 seed fuzzy basis | 11.6 | 11.6 |
| Lint Index | g lint/100 seeds | 7 | 7.1 |
| Boll | | | |
| Lint percent, picked | | 37 | 38 |
| Gin Turnout, stripped | | | |
| Number of Seeds per Boll | | 27.9 | 34.4 |
| Grams Seed Cotton per Boll | | 5.4 | 6.8 |
| Number of Locules per Boll | | 4.3 | 4.3 |
| Boll Type | storm proof, storm resistant, open | Storm Resistant | Storm Resistant |
| Fiber Properties Method HVI | | | |
| Length, inches, 2.5% SL | | 1.19 | 1.13 |
| Uniformity (%) | | 84.9 | 83.1 |
| Strength, T1 (g/tex) | | 33.5 | 34.5 |
| Elongation, E1 (%) | | 8.2 | 8.1 |
| Micronaire | | 4.8 | 4.8 |
| Diseases, Insects and Pests | | | |
| Bacterial Blight race 1 | susceptible = S, moderately susceptible = MS | R | |
| Bacterial Blight race 2 | moderately resistant = MR, resistant = R | R | |
| Bacterial Blight Race 18 | | R | |
| Fusarium Wilt | | MS | |
| Verticillium Wilt | | MR | |
| Root-Knot Nematode | | MS | |
| Bollworm | | R | |
| Cotton Leafworm | | | |
| Fall Armyworm | | | |
| Pink Bollworm | | | |
| Tobacco Budworm | | | |

Example 2

A variety that has been essentially derived from FM 9063B2F by the process of the transgression of the Event LLCotton 25, USDA-APHIS petition 02-042-01p, U.S. Pat. No. 6,818,807, into plants of the variety FM 9063B2F via the method of recurrent backcrossing and selecting the plants which express the characteristics of FM 9063B2F combined with the resistance to the herbicide glyfosinate.

Example 3

A variety that has been essentially derived from FM 9063B2F by the process of the transgression of the Event LLCotton 25 via genetic engineering in regenerable cells or tissue of FM 9063B2F and the subsequent selection of regenerated plants, which express the characteristics of FM 9063B2F combined with the resistance to the herbicide glyfosinate.

Example 4

A variety that has been essentially derived from FM 9063B2F by the selection of an induced or natural occurring mutant plant or off-type plant from plants of FM 9063B2F, which plant retains the expression of the phenotypic characteristics of FM 9063B2F and differs only from FM 9063B2F in the expression of one, or two, or three, or four, or five of the characteristics as listed in table 1 and when grown side by side with FM 9063B2F on one or two locations in one or two growing seasons.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Seed of cotton variety FM 9063B2F of which a representative seed sample has been deposited under ATCC Patent Deposit Designation No. PTA-12471.

2. Plants, or parts thereof, produced by growing the seed of claim 1 and expressing all the phenotypic characteristics of cotton variety FM 9063B2F that are the result of the genotype of FM 9063B2F.

3. Seed produced by plants of claim 2.

4. Plants, or parts thereof obtained by vegetative reproduction from plants, or parts thereof, of claim 2, expressing all the phenotypic characteristics of cotton variety FM 9063B2F that are the result of the genotype of FM 9063B2F.

5. A method comprising sexually or vegetatively reproducing cotton variety FM 9063B2F.

6. Cotton lint harvested from plants of claim 2 or claim 4 or cotton fiber obtained therefrom.

7. A cell or tissue culture produced from plants or parts thereof of claim 2 or claim 4.

8. A cotton plant regenerated from the cell or tissue culture of claim 7, which expresses all the phenotypic characteristics of FM 9063B2F that result from the genotype of FM 9063B2F.

9. A method of producing F1 hybrid cotton seed, comprising the steps of crossing plants of claim 2 with cotton plants distinct from FM 9063B2F and harvesting the resultant F1 hybrid cotton seed.

10. F1 hybrid cotton seed produced by the method of claim 9.

11. F1 Hybrid cotton plants, or parts thereof, produced by growing the hybrid seed of claim 10.

12. Plants obtained by the vegetative reproduction of the cotton plants of claim 11, expressing all the phenotypic characteristics of the plant of claim 11.

13. A method of producing F1 cotton seed comprising the steps of crossing plants of claim 11 or 12 with cotton plants different from those plants of claim 11 or 12 and harvesting the resultant F1 hybrid cotton seed.

14. A method of producing essentially derived cotton plants from FM 9063B2F, comprising adding a desired trait through genetic transformation in regenerable plant tissue or plant cell tissue of claim 7, which essentially derived plants retain the expression of all the phenotypic characteristics of cotton variety FM 9063B2F that are the result of the genotype of FM 9063B2F, and one, or two, or three, or four, or five characteristics have been introduced by this method of essential derivation.

15. A method of producing essentially derived cotton plants from FM 9063B2F, comprising the steps of crossing the plant of claim 2 with a distinct cotton plant and backcrossing the resulting plants at least two times with the plant of claim 2 as the recurrent parent, to introduce a desired trait in FM 9063B2F, said essentially derived cotton plants retaining the expression of all the phenotypic characteristics of FM 9063B2F that are the result of the genotype of FM 9063B2F, and one, or two, or three, or four, or five phenotypic characteristics have been introduced by this method of essential derivation.

16. The method of claim 14 wherein said desired trait is selected from the group consisting of modified cotton fiber characteristics, herbicide tolerance, insect resistance, bacterial disease resistance, fungal disease resistance, male sterility, modified carbohydrate metabolism and modified fatty acid metabolism.

17. The method of claim 14 wherein the desired trait is herbicide tolerance and the tolerance is conferred to a herbicide selected from the group consisting of glyphosate, glufosinate, sulfonylurea, dicamba, phenoxy proprionic acid, cycloshexone, triazine, benzonitrile, bromoxynil and imidazalinone.

18. The method of claim 16 wherein
  (a) the desired herbicide tolerance is an expression of a bar coding sequence from *Streptomyces hygroscopicus* encoding phosphinothricin-acetyl-transferase, operably linked to a cauliflower mosaic virus 35S promoter and 3' untranslated region from a nopaline synthase gene.

19. A method of producing essentially derived cotton plants from FM 9063B2F, comprising the steps of selecting a naturally occurring or induced mutant of the plants of claim 2 to change a trait of FM 9063B2F into a desired or different trait, and which essentially derived plants retain the expression of all phenotypic characteristics of cotton variety FM 9063B2F that are the result of the genotype of FM 9063B2F, except for one, or two, or three, or four, or five characteristics that have been changed by the method of essential derivation.

20. Plants or parts thereof or and seed produced by those plants, obtained by the method of claim 14 and retaining the expression of all the phenotypic characteristics of cotton variety FM 9063B2F.

21. A method of producing a cotton plant derived from cotton variety FM 9063B2F, comprising the steps of:
  a) crossing the plant of claim 2 with another cotton plant distinct from the plant of claim 2,
  b) growing the resulting F1 seed under plant growing conditions and crossing the resulting F1 plant with itself or with another, distinct cotton plant, c) growing the resulting progeny seed of step b) under plant growing conditions and crossing the resulting progeny plant with itself or with another, distinct cotton plant,
d) repeating step c) for 0 to 8 times to produce a FM 9063B2F derived cotton plant.

22. Cotton lint or fiber obtained from the plants of claim 20.

23. The method of claim 15 wherein said desired trait is selected from the group consisting of modified cotton fiber characteristics, herbicide tolerance, insect resistance, bacterial disease resistance, fungal disease resistance, male sterility, modified carbohydrate metabolism and modified fatty acid metabolism.

24. The method of claim 15 wherein the desired trait is herbicide tolerance and the tolerance is conferred to a herbicide selected from the group consisting of glyphosate, glufosinate, sulfonylurea, dicamba, phenoxy proprionic acid, cycloshexone, triazine, benzonitrile, bromoxynil and imidazalinone.

25. The method of claim 23 wherein
(a) the desired herbicide tolerance is an expression of the a bar coding sequence from Streptomyces hygroscopicus encoding phosphinothricin-acetyl-transferase, operably linked to a cauliflower mosaic virus 35S promoter and 3' untranslated region from a nopaline synthase gene.

26. Seed produced by the plants of claim 20.

27. Plants, or parts thereof, grown from the seed of claim 26.

28. Plants, or parts thereof, obtained by the method of claim 15.

29. Seed produced by the plants of claim 28.

30. Plants, or parts thereof, grown from the seed of claim 29.

31. Cotton lint or fiber obtained from the plants of claim 28.

32. Plants, or parts thereof, obtained by the method of claim 19.

33. Seed produced by the plants of claim 32.

34. Plants, or parts thereof, obtained by growing the seed of claim 33.

35. Cotton lint or fiber obtained from the plants of claim 32.

36. The method of claim 16 wherein the herbicide tolerance is an expression of a bar coding sequence from , Streptomyces hygroscopicus encoding phosphinothricin-acetyl-transferase, operably linked to a cauliflower mosaic virus 35S promoter and 3' untranslated region from a nopaline synthase gene.

* * * * *